Figure 1:
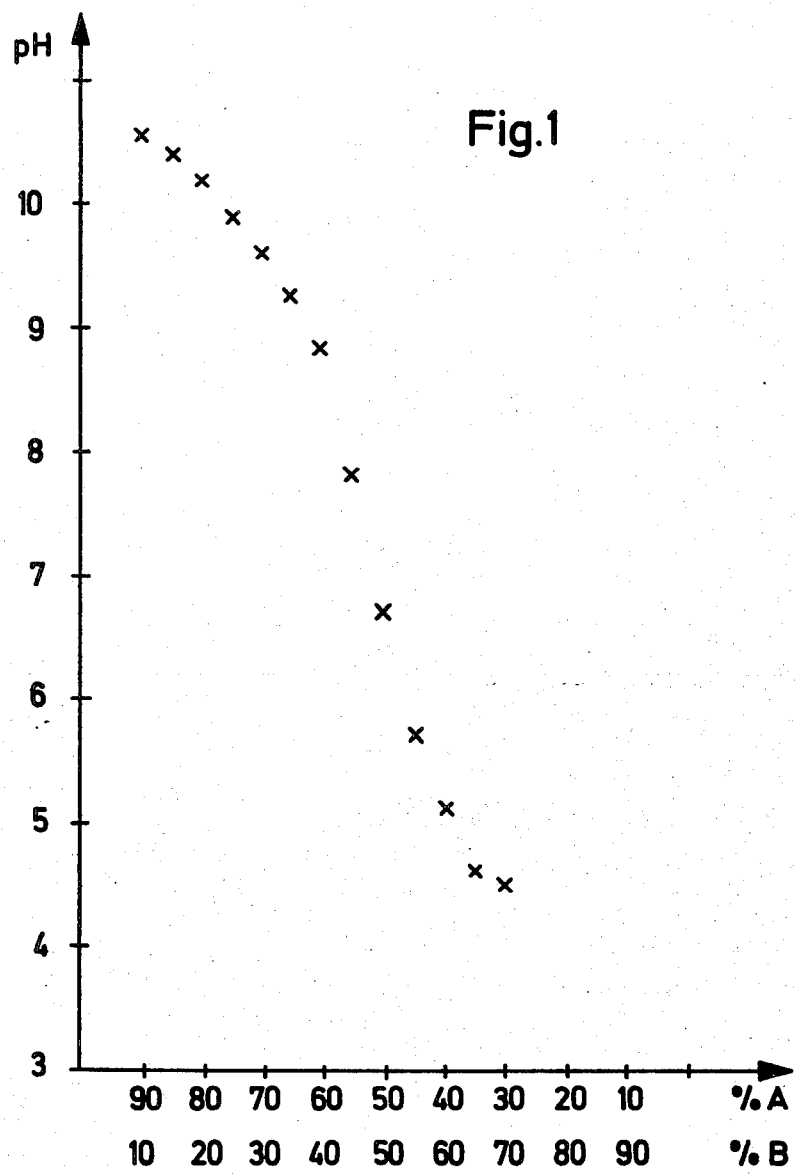

United States Patent [19]

Just

[11] 4,131,534
[45] Dec. 26, 1978

[54] PREPARATION OF CARRIER AMPHOLYTE MIXTURES

[75] Inventor: Wilhelm Just, Frankfurt am Main, Fed. Rep. of Germany

[73] Assignee: Max-Planck-Gesellschaft zur Foederung der Wissenschaften e.V., Munich, Fed. Rep. of Germany

[21] Appl. No.: 860,615

[22] Filed: Dec. 14, 1977

[30] Foreign Application Priority Data

Dec. 15, 1976 [DE] Fed. Rep. of Germany ....... 2656801

[51] Int. Cl.² ............................................ G01N 27/26
[52] U.S. Cl. .......................... 204/299 R; 204/180 R; 204/180 G; 204/180 S; 252/62.2; 560/205; 560/190; 560/171; 260/404; 260/404.5

[58] Field of Search ........... 204/180 R, 180 S, 180 G; 252/62.2; 560/205, 190, 171; 260/404, 404.5

[56] References Cited

U.S. PATENT DOCUMENTS

| | | | |
|---|---|---|---|
| 3,485,736 | 12/1969 | Vesterberg | 204/180 R |
| 3,692,654 | 9/1972 | Svendsen | 204/180 R |
| 3,901,780 | 8/1975 | Denckla | 204/180 R |

*Primary Examiner*—Arthur C. Prescott
*Attorney, Agent, or Firm*—Cooper, Dunham, Clark, Griffin & Moran

[57] ABSTRACT

Carrier ampholyte mixtures are prepared by reaction between organic amino or imino compounds and unsaturated carboxylic acid esters followed by hydrolysis.

19 Claims, 2 Drawing Figures

PREPARATION OF CARRIER AMPHOLYTE MIXTURES

BACKGROUND OF THE INVENTION

The present invention is concerned with a new synthesis procedure for the preparation of novel carrier ampholyte mixtures suitable for isoelectric focusing of high molecular weight amphoteric substances (e.g., proteins).

During the process of stationary electrolysis, carrier ampholytes generate a uniform pH-gradient between the anode and the cathode. Preferentially, such carrier ampholyte mixtures consist of multiple chemical substances which differ from each other by the nature and the number of basic and acidic groups and, therefore, each ampholyte species has its own isoelectric point. In a particularly suitable system of carrier ampholytes, the isoelectric points of the different ampholyte species will cover the p-range 3–10 because most of the naturally occurring proteins are isoelectric within that pH-range.

Substantially uniform distribution of the isoelectric points of the various ampholyte species throughout the desired pH-range is an important factor for the formation of uniformly and linearly developed pH-gradients.

U.S. Pat. No. 3,485,736 describes a procedure for the synthesis of a mixture of polyamino-polycarboxylic acids suitable as carrier ampholytes for isoelectric focusing. This procedure utilizes a polyethylene-polyamine to which an, $\alpha,\beta$-unsaturated acid, e.g., acrylic acid, is chemically linked by an addition reaction. The simplest ampholyte formed by that reaction is a polyethylene-polyamine molecule to which one carboxylic acid molecule is linked forming a $\beta$-aminocarboxylic acid group. Thereafter, $\beta$-aminopolycarboxylic acids are obtained containing an increasing number of carboxylic acid groups in the molecule. The method of synthesis makes use of a known procedure of organic chemistry. To the aqueous solution of the polyethylene-polyamine a certain empirically determined amount of the aqueous solution of the carboxylic acid is added with simultaneous heating and stirring.

Under these conditions, obviously some of the ampholyte species which are more susceptible to the chemical reaction are obtained in higher yield whereas others will be formed in relatively low amounts. A suitable carrier ampholyte mixture forming a pH-gradient, however, should exhibit a uniform distribution of buffering capacity and conductivity throughout the pH-gradient. This is only achieved when the different carrier ampholyte species are contained in the mixture in about the same concentrations. Therefore, at the end of the chemical reaction, a fractionation of the carrier ampholyte mixture in an expansive multicompartment electrolysis equipment is necessary. A useful carrier ampholyte mixture is obtained by mixing appropriate amounts of materials from different electrolysis compartments.

Since the addition reaction between the unsaturated carboxylic acid and the polyethylene-polyamine exhibits very slow reaction kinetics at room temperature, the reaction is performed at elevated temperature. This, however, leads to undesired side products which cause coloration of the end product. Additionally, even at elevated temperature, the reaction knetics are rather slow and it is difficult to cause all of the unsaturated carboxylic acid to react. Such reaction, however, is essential to avoid artefacts during the isoelectric focusing procedure which may be caused by reaction of the unreacted unsaturated carboxylic acid with functional groups of proteins. For all these reasons, the known procedure is not completely satisfactory, and the art has searched for improvements.

THE INVENTION

A process has now been discovered for the synthesis of carrier ampholyte mixtures by initially reacting at least one organic compound substituted with at least two amino or imino groups and at least one unsaturated carboxylic acid ester containing a double bond which is activated for addition reactions by the electronic structure of the molecule. The novel amino-carboxylic acid ester mixture which is produced is then hydrolyzed, i.e., reacted with water, to form the ampholyte mixture and alcohol.

Instead of one single amine, amine mixtures may be used and instead of one single carboxylic acid ester, a mixture of several esters containing at least one carbon-carbon double bond within their molecules may be utilized.

The present procedure has advantages over the known method in that the caarboxylic acid esters surprisingly exhibit much faster reaction kinetics than the corresponding carboxylic acids. Therefore, the process of the present invention involves appreciable time saving. Furthermore, the present procedure may be performed at room temperature or at only slightly elevated temperature. Any weak yellow coloration which may form is readily removed by treating the product with hydrogen in the presence of a suitable catalyst, e.g., a noble metal catalyst.

The procedure may be performed by adding the carboxylic acid ester dropwise to the total amount of amine. Preferentially, the reaction is performed by adding increasing concentrations of the one component (e.g., the carboxylic acid ester) to decreasing concentrations of the other component (e.g., the amine mixture) or by adding to the constant concentration of the one component increasing or decreasing concentrations of the other component. This is done in such a way that the synthesized amino-carboxylic acid esters after hydrolysis to the corresponding amino-carboxylic acids and subjecting the ampholytes to stationary electrolysis form a practically linear pH-gradient. A particular advantage of the process of this invention is that the various ampholyte species are formed directly in approximately the same proportions. Therefore, the laborious fractionation of the synthesized carrier ampholyte mixture is avoided.

The use of $\alpha,\beta$-unsaturated esters instead of carboxylic acids is furthermore advantageous in that the different nitrogen atoms within the amine molecules which exhibit highly different pK-values will not change their state of charge, i.e., they will not become protonated during the synthesis as will be the case using the free acids. The protonated nitrogen will hardly undergo any addition reaction. Moreover, the present procedure provides the advantage that unreacted unsaturated ester may be quantitatively removed in vacuum.

Another significant advantage of the present procedure is given by the possibility of synthesizing ampholyte mixtures which, when subjected to stationary electrolysis, produce pH-gradients of selected pH-ranges. Ampholyte mixtures which cover the pH-range 8–10 or 4–7 were successfully synthesized by the process of this invention. The maximum pI-spectrum of the carrier ampholyte mixture obtained by the reaction of pentaethylenehexamine and acrylic acid methyl ester covers the pH-range 3.5-10. Since a restricted pH-range is produced over the same distance between the anode and the cathode, the use of selected, restricted pH-ranges leads to a higher resolution of proteins with closely spaced isoelectric points. Therefore, restricted pH-ranges play an important role in the fractionation of proteins by isoelectric focusing.

The organic compounds which are employed for the synthesis of carrier ampholytes should contain at least two amino and/or imino groups. Preferably, this will contain at least four nitrogen atoms within the molecule to which the carboxylic acid esters are linked. This provides a higher number of individual carrier ampholytes in the synthesized mixture, each of them exhibiting a different isoelectric point. Amines which are suitable for the present procedure are composed of the following unit: —NH—R—NH—.

The chain length may be prolonged to both directions with similar units (—R—NH—) in such a way that the resulting compounds have preferably a molecular weight of about 300–500. However, for special purposes the resulting compounds may have molecular weights of up to 20,000 and more. In the above formula, R is —$C_3H_6$— or preferably —$C_2H_4$—. Typically, these organic nitrogen compounds will be linear chain molecules. However, compounds containing branched chains as well as alicyclic, heterocyclic or aromatic groups may also be useful. Moreover, various nitrogen atoms may be substituted by alkyl groups which may contain 1 to 6 carbon atoms. Suitable amines, for example, are diethylenetriamine, triethylenetetramine and tetraethylenepentamine. In particular, pentaethylenehexamine is preferred.

The carboxylic acid esters which are used according to the present invention contain an activated carbon-carbon double bond. Carboxylic acid esters with a double bond in the $\alpha,\beta$-position are preferably used although the double bond may be positioned elsewhere within the molecule and may then be activted otherwise. The carboxylic acid esters may contain up to 10–12 carbon atoms; the alcoholic component of the ester up to 6, preferably, not more than 4 carbon atoms.

Suitable carboxylic acid esters are acrylic acid ester, methacrylic acid ester, crotonic acid ester, etc. Furthermore, unsaturated dicarboxylic acid esters such as maleic acid esters, methylene malonic acid esters, ethylene malonic acid esters, itaconic acid esters, etc., are suitable for special purposes. This is in fact another important advantage of the present procedure since the use of the unsaturated dicarboxylic acids produces a further decrease of the reaction velocity compared with the monocarboxylic acids whereas the dicarboxylic acid esters react quite promptly. In addition, the present procedure allows the use of compounds such as methylene malonic acid ester which is known to be stable only in the esterified form.

Preferably, the alcoholic component of the esters is methyl, ethyl, propyl, isopropyl, n-butyl, sec.-butyl, or tert.-butyl alcohol. Particularly preferred is methyl alcohol.

The reaction takes place in an anhydrous organic solvent, preferably an alcoholic solution. Methyl, ethyl, propyl, isopropyl, n-butyl, sec.-butyl, or tert.-butyl alcohol are used. Particularly preferred is methyl alcohol. Other water-free organic solvents such as benzene or dioxan, etc., which are chemically inert under the reaction conditions, are also suitable for the synthesis.

For the controlled synthesis of a carrier ampholyte mixture of the present invention, gradual mixing of the starting materials is employed. These mixing ratios may be calculated with good accuracy from known physico-chemical parameters. The determination of these parameters and the calculation of the resulting mixing ratios are explained in the example. After evaluation of these mixing ratios, the starting materials, preferably dissolved in alcoholic solvents, are either mixed by hand stepwise in several fractions or continuously by means of a gradient former device. Such equipment is commercially available and in general is used for the formation of gradients for density gradient centrifugation or chromatographic elution procedures.

Using a gradient former (Ultrograd gradient mixer, LKB, Bromma, Sweden), the mixture which is continuously altered in its composition is pumped through a teflon tubing of 10–20 m length which is contained in a thermostated water bath in which the temperature is adjusted to 0–50° C, preferably, to 30–40° C. The pumping rate of the peristaltic pump is regulated so that the continuously produced mixtures remain at least 1.5–2 hours within the tubing. This guarantees that the reaction is substantially completed. After the flow through the teflon tubing, the mixture is collected in several fractions at 30–40° C for several hours. The fractions are then combined and the solvent removed by evaporation in the vacuum. Small amounts of unreacted ester are removed simultaneously.

Following decomposition of the obtained residue in a sufficient amount of water, the cleavage of the ester bonds may be achieved by different ways. The hydrolysis may be accomplished in a sterilizer at a pressure of 1–2 atmospheres at 120–130° C for about 2 hours. Another possibility is the performance of the hydrolysis at 40–50° C in an agitated water bath. The last procedure resulted in an end product exhibiting especially low absorption in the visible and ultraviolet region of the spectrum.

As already mentioned, the present procedure produces a carrier ampholyte mixture which may have a slight yellow coloration. To remove that coloration and to lower the absorption in the ultraviolet region of the spectrum, the carrier ampholyte mixture is treated with hydrogen in the presence of a suitable catalyst. Raney-nickel, platinum oxide, palladium, or palladium/activated carbon or hydrides such as lithium aluminum hydride and sodium boron hydride may be used. The hydrogenation is preferably performed in aqueous solution but may also be carried out in a suitable organic solvent.

The following non-limiting example is given by way of illustration only.

EXAMPLE

Starting Materials:

1. Pentaethylenehexamine, 1 molar solution in methanol, hereinafter designated as solution A.

2. Acrylic acid methyl ester, 4 molar solution in methanol, hereinafter designated as solution B.

In the following, percentage concentrations are used which are to be understood as volume-%.

The pentaethylenehexamine starting material contains 6 nitrogen atoms in the molecule to which a maximum of 8 carboxylic acid ester molecules may be linked. Therefore, the simplest ampholyte is formed by reacting the amine and carboxylic acid ester solutions in a molar ratio of 1:1. Using the solutions A and B, this 1:1 ratio is obtained when A and B are mixed in the percentage concentration ratio of 80:20, respectively. This ratio, therefore, represents the starting ratio for the synthesis. The final ratio at which the synthesis is completed is reached at a molar ratio of the amine and carboxylic acid ester solutions of 1:8, or at a percentage ratio of the solutions A and B of 35:65, respectively.

Starting from the percentage ratio of 80:20, 10 or more individual fractions are prepared changing the ratio gradually until reaching the final ratio of 35:65. The fractions are stored at 35° C for 2 hours. The solvent is removed in the vacuum and the residue, after dissolution in water, is hydrolyzed for 2 hours at 130° C in a sterilizer. The pH of the various fractions is plotted versus the percentage ratios of the solutions A and B. The curve obtained (FIG. 1) is used for the computation of the templet which directs the gradient former. A slight correction must be taken into account. At any time during the synthesis, the amine concentration governs the number of synthesized ampholytes. Since the amine concentration decreases during the synthesis, fewer acidic than basic ampholytes are formed. Using the gradient former, this correction can be made in either of two ways:

1. The speed of the peristaltic pump may be increased synchronously with the decrease of the amine concentration.
2. The curve which determines the mixing ratios of solutions A and B obtained from the curve shown in FIG. 1 is modified in such a way that with decreasing concentrations of the amine more time is available for the production of the actual percentage ratios of solutions A and B.

Figure 2:
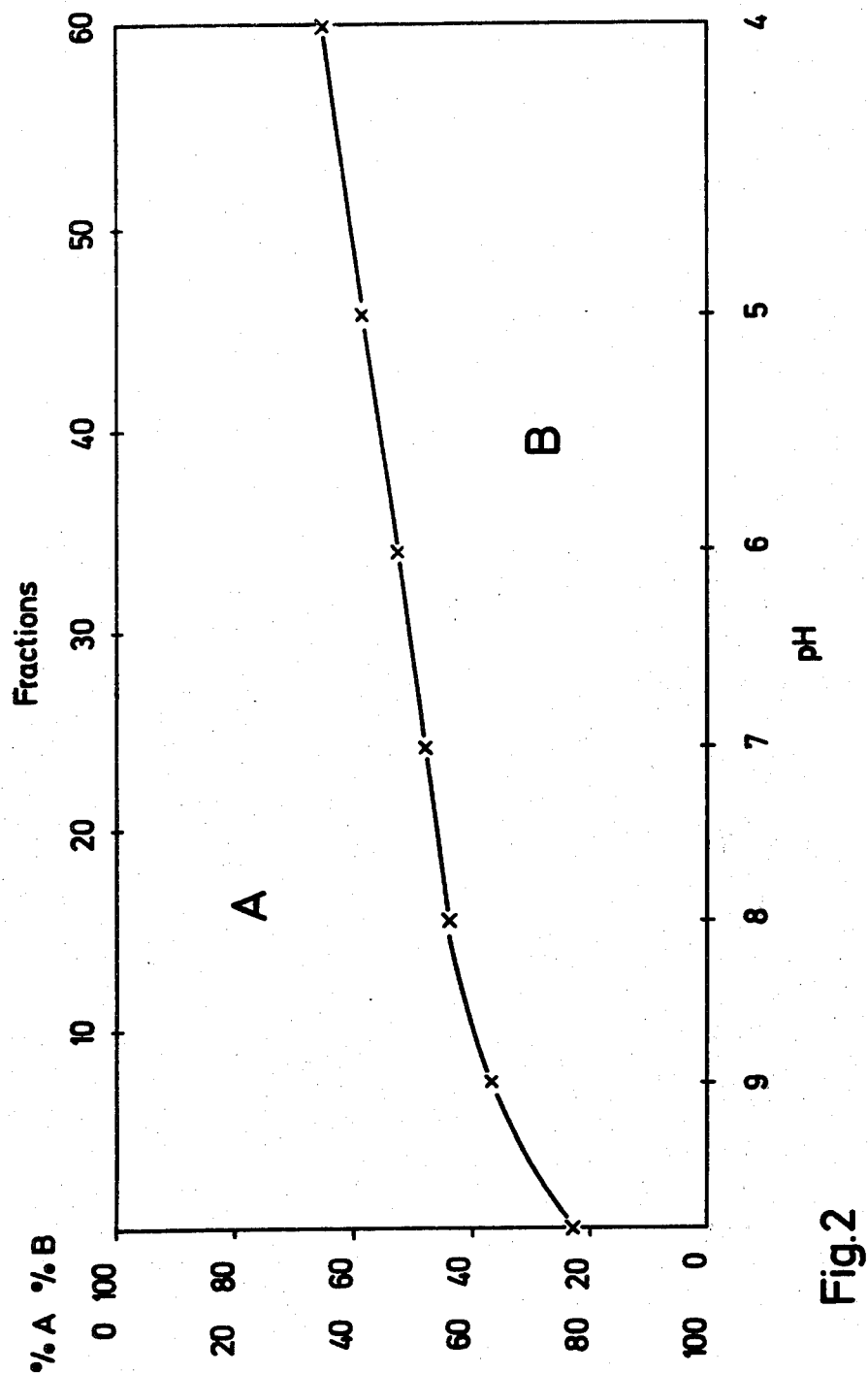

For the present example, the second procedure is selected. The curve shown in FIG. 1 allows for the correlation of the percentage mixing ratios and pH-values of the synthesized ampholytes. From the decrease of the amine concentration per pH-unit, a factor is easily calculated giving the time prolongation for the mixing process in the actual pH-range. Applying this correction, it is established that for each pH-range approximately the same number of carrier ampholytes is produced. FIG. 2 shows the final templet for the gradient former.

The same result is also obtained when increasing concentrations of carboxylic acid ester are added to constant concentrations of the amine. A curve equivalent to that shown in FIG. 2 should be obtained which now needs no correction because of the constant amine concentration.

According to the curve shown in FIG. 2, several fractions may be prepared by hand (therefore, the abscissa of the graph is divided into 60 fractions) or the curve may serve directly as a templet for the gradient former. The latter case is applied in this example.

The starting solutions A and B are contained in 100 ml vessels which are connected with an electrically controlled ventil system. A peristaltic pump on the one side pumps the solutions A and B, according to the ventil activity which is governed by the templet of FIG. 2, into a mixing chamber and pumps the mixture on the other side through the teflon tubing (10 m length, 1 mm diameter) which is contained in a thermostated water bath adjusted to 40° C. After passing the teflon tubing, the mixture is collected in about 60 fractions, each containing about 2 ml of solution. The pumping velocity is adjusted to 0.5 ml/min. About 70 ml of the solutions A and B are consumed. The fractions are sealed and stored for two hours at 35° C. They are combined and after removal of the solvent they are hydrolyzed and hydrogenated as described above. The aqueous solution is lyophilized yielding 35-40 g of almost colorless crystals. When subjected to stationary electrolysis, the ampholyte mixture forms a completely linear pH-gradient covering the pH-range 3.5-10.

The procedure for determining the curve shown in FIG. 2 using pentaethylenehexamine, as illustrated in this example, is similarly employed for other amines.

What is claimed is:

1. A process for the synthesis of a carrier ampholyte mixture which comprises first reacting at least one organic compound substituted with at least two amino or imino groups and at least one unsaturated carboxylic acid ester containing an activated double bond in an anhydrous organic solvent at a temperature of from about 0° C to 50° C to produce a mixture of amino-carboxylic acid esters and thereafter hydrolyzing the esters to produce a mixture of amino-carboxylic acids; the carboxylic acid moiety of the unsaturated carboxylic acid ester being aliphatic and containing up to 12 carbon atoms; the ester moiety being aliphatic and containing up to 6 carbon atoms.

2. A process according to claim 1 wherein the first reaction is carried out by adding increasing concentrations of one reactant to decreasing concentrations of the other reactant.

3. A process according to claim 1 wherein the reaction is carried out by maintaining the concentration of one reactant constant while adding increasing or decreasing concentrations of the other reactant.

4. A process as in claim 1 wherein the solvent is an alcohol containing up to four carbon atoms.

5. A process according to claim 1 wherein the organic compound is selected from the group consisting of diethylenetriamine, triethylenetetramine, tetraethylenepentamine and pentaethylenehexamine.

6. A process according to claim 1 wherein the ester is an ester of an acid selected from the group consisting of acrylic, methacrylic, methylenemalonic, ethylenemalonic, crotonic, maleic, fumaric, and itaconic.

7. A process according to claim 1 wherein the ester moiety contains an alkyl group selected from the group consisting of methyl, ethyl, propyl, isopropyl, n-butyl, sec. butyl and tert. butyl.

8. A process according to claim 1 wherein at least two organic compounds substituted with at least two amino or imino groups are employed.

9. A process according to claim 1 wherein at least two unsaturated carboxylic acid esters are employed.

10. A process according to claim 1 wherein the first reaction is conducted by initially preparing several fractions containing different ratios of each reactant and thereafter contacting the several fractions at a temperature of from about 0° C to 50° C.

11. A process according to claim 1 wherein the solvent is selected from the group consisting of benzene and methyl, ethyl, propyl, isopropyl, n-butyl, sec. butyl and tert. butyl alcohols.

12. A process according to claim 1 wherein the reaction temperature is from 0 to 40° C.

13. A process according to claim 1 wherein the hydrolyzed mixture is decolorized by hydrogenation utilizing a catalyst selected from the group consisting of raney nickel, platinum oxide, palladium, and palladium in activated carbon.

14. A process according to claim 1 wherein the hydrolyzed mixture is decolorized by hydrogenation utilizing a hydride selected from the group consisting of lithium aluminum hydride and sodium boron hydride.

15. An amino-carboxylic acid ester mixture comprising the reaction product of at least one organic compound substituted with at least two amino or imino groups and at least one unsaturaged carboxylic acid ester containing an activated double bond in an anhydrous organic solvent at a temperature from about 0° C to 50° C; the carboxylic acid moiety of the unsaturated carboxylic acid ester being aliphatic and containing up to 12 carbon atoms; the ester moiety being aliphatic and containing up to 6 carbon atoms.

16. A product of claim 15 wherein the organic compound is selected from the group consisting of diethylenetriamine, triethylenetetramine, tetraethylenepentamine, and pentaethylenehexamine.

17. A product of claim 15 wherein the ester is an ester of an acid selected from the group consisting of acrylic, methacrylic, methylenemalonic, ethylenemalonic, crotonic, maleic, fumaric, and itaconic.

18. A product of claim 15 wherein the ester moiety contains an alkyl group selected from the group consisting of methyl, ethyl, propyl, isopropyl, n-butyl, sec. butyl, and tert. butyl.

19. A product of claim 15, having a molecular weight up to 20,000 and more.

* * * * *